United States Patent

Joo et al.

[11] Patent Number: 6,130,362
[45] Date of Patent: Oct. 10, 2000

[54] METHOD FOR PREPARING ETHYLBENZENE FROM 4-VINYLCYCLOHEXENE

[75] Inventors: Young J. Joo; Jeong-Im Won, both of Taejeon; Kwang-Chun Park, Chollanam-do; Chang-Min Kim, Taejeon, all of Rep. of Korea

[73] Assignee: Korea Kumho Petrochemical Co., Ltd., Seoul, Rep. of Korea

[21] Appl. No.: 08/776,459

[22] PCT Filed: May 25, 1996

[86] PCT No.: PCT/KR96/00076

§ 371 Date: Jan. 14, 1997

§ 102(e) Date: Jan. 14, 1997

[87] PCT Pub. No.: WO96/37449

PCT Pub. Date: Nov. 28, 1996

[30] Foreign Application Priority Data

May 25, 1995 [KR] Rep. of Korea ................ 95/13184
Aug. 16, 1995 [KR] Rep. of Korea ................ 95/25189
Nov. 10, 1995 [KR] Rep. of Korea ................ 95/40588

[51] Int. Cl.$^7$ ........................................... C07C 5/41
[52] U.S. Cl. ................ 585/434; 589/434; 589/431; 589/443; 589/419; 589/444; 585/535
[58] Field of Search ................ 585/434, 431, 585/443, 419, 444, 435

[56] References Cited

U.S. PATENT DOCUMENTS

| | | |
|---|---|---|
| 4,233,244 | 11/1980 | Patterson . |
| 4,239,928 | 12/1980 | Takahashi et al. .............. 585/431 |
| 4,246,202 | 1/1981 | Cihonski . |
| 4,300,010 | 11/1981 | Cihonski . |
| 4,339,622 | 7/1982 | Patterson . |
| 4,375,571 | 3/1983 | Hart . |
| 5,096,870 | 3/1992 | Heaton . |
| 5,196,621 | 3/1993 | Diessen et al. . |
| 5,276,257 | 1/1994 | Diessen . |
| 5,300,719 | 4/1994 | Diessen . |
| 5,321,180 | 6/1994 | Davis . |
| 5,329,057 | 7/1994 | Diessen et al. . |
| 5,336,822 | 8/1994 | Hucul . |

FOREIGN PATENT DOCUMENTS

| | | | |
|---|---|---|---|
| 6172238 | 6/1994 | Japan | ............ C07C 33/14 |
| 6247880 | 6/1994 | Japan | ............ C07C 13/20 |
| 6329563 | 11/1994 | Japan | ............ C07C 15/073 |
| 741436 | 2/1995 | Japan | ............ C07C 15/073 |
| 748288 | 2/1995 | Japan | ............ C07C 13/20 |
| 748289 | 2/1995 | Japan | ............ C07C 13/20 |
| 748290 | 2/1995 | Japan | ............ C07C 13/20 |
| 9401385 | 1/1994 | WIPO | ............ C07C 15/073 |
| 9408925 | 4/1994 | WIPO | ............ C07C 13/20 |
| 9410111 | 5/1994 | WIPO | ............ C07C 15/073 |
| 9429248 | 12/1994 | WIPO | ............ C07C 15/46 |

*Primary Examiner*—Glenn Caldarola
*Assistant Examiner*—Bekir L. Yildirim
*Attorney, Agent, or Firm*—Harrison & Egbert

[57] ABSTRACT

In the presence of a heterogeneous catalyst made of palladium supported on active carbon, ethylbenzene is prepared from 4-vinylcyclohexene through catalytic transfer hydrogenation in a hydrogen donor solvent with an oxidizing agent. Reaction temperature ranges from 50 to 110° C. The hydrogen donor solvent is selected from the group consisting of alcohol, water, and a mixture of these. The oxidizing agent is selected from monovalent or divalent nitro compounds, water, hydrogen peroxide, NaOCl, NaClO$_2$, NaClO$_3$, NaClO$_4$, oxygen and air, and used in the amount of 0.02 to 3 moles per mole of 4-vinylcyclohexene.

10 Claims, No Drawings

METHOD FOR PREPARING ETHYLBENZENE FROM 4-VINYLCYCLOHEXENE

This application is a 371 of PCT/KR96/00076 filed May 25, 1996.

BACKGROUND OF THE INVENTION

1. Field of the Invention

The present invention relates, in general, to a method for preparing ethylbenzene from 4-vinylcyclohexene (hereinafter referred to as "4-VCH") through catalytic transfer hydrogenation. More particularly, the present invention is concerned with a method for preparing ethylbenzene in which 4-VCH is dehydrogenated in a hydrogen donor solvent with an oxidative dehydrogenation agent in the presence of palladium supported on active carbon as a heterogeneous catalyst.

2. Description of the Prior Art $C_4$ fraction which contains 1,3-butadiene in an economically isolable content is available in countries where ethylene is manufactured by steam cracking of naphtha. This $C_4$ fraction contains by weight about 45 wt % of 1,3-butadiene and the remainder is butanes, butenes and butynes. 1,3-Butadiene from mixed $C_4$ hydrocarbons is not capable of separation of simple distillation because boiling points of all components have very close temperature ranges, and some components form azeotropic mixtures.

All modern processes from isolating 1,3-butadiene are based on the physical principle of extractive distillation, and 1,3-butadiene is usually used for the production of synthetic rubbers. During the extractive distillation process, storage, or transfer, 1,3-butadiene is dimerized into 4-VCH through [2+4] Diels-Alder reaction. Currently, the produced amount of 4-VCH is approximately 1% of that of 1,3-butadiene and the whole quantity thereof is burnt. Since the by-product, 4-VCH, is increased with 1,3-butadiene, the industrial use of 4-VCH is becoming a new field of research.

Up to the present, 4-VCH had been recognized industrially as an almost useless compound. In the 1970s, there was research for the preparation of ethylbenzene or styrene from 4-VCH using oxidative dehydrogenation. However, since 1,3-butadiene, the raw material of 4-VCH, was in short supply owing to the great demand for synthetic rubbers, and moreover was expensive. The research for the oxidative dehydrogenation of 4-VCH was shown in only some documents, including U.S. Pat. Nos. 4,163,761 (1979), 4,233,244 (1980), 4,246,202 (1981), 4,300,010 (1981), 4,322,566 (1982), 4,339,622 (1982) and 4,375,571 (1983). Since the mid-1980s, there has been little research done on this topic.

More than 90% of 1,3-butadiene has been used to produce synthetic rubbers. Recently, the demand for synthetic rubbers has grown dull, but the supply of 1,3-butadiene has increased. Accordingly, [2+4] Diels-Alder reaction and dehydrogenation for 1,3-butadiene are now being actively studied with the aim of utilizing 1,3-butadiene for purposes other than synthetic rubbers, as disclosed in Applied Catalysis, 47(1989), L7-L8. Particularly, active research for the dehydrogenation of 4-VCH has been done with the hope of commercial success. As evidence, many patents have been published in 1944, including U.S. Pat. No. 5,276,257, (1994), 5,300,719 (1994), 5,321,180 (1994) and 5,336,822 (1994), Japanese Pat. Laid-Open Publication Nos. Heisei 6-329563 and Heisei 7-41436, and PCT Nos. 94/01385 and 94/29248. It is highly expected that the dehydrogenation of 4-VCH would contribute to the utilization of 1,3-butadiene, which is anticipated to be in excess supply, as well as 4-VCH. 4-VCH is prepared from 1,3-butadiene, as disclosed in U.S. Pat. Nos. 5,096,870 (1992), 5,196,621, (1993) and 5,329,057 (1994), Japanese Pat. Laid-Open Publication Nos. Heisei 6-172238 (1994), Heisei 6-247880 (1994), Heisei 7-48288 (1995), Heisei 7-48289 (1995), and Heisei 7-48290 (1995), and PCT 94/008925. With greater progress in theory, the preparation methods of 4-VCH disclosed in these recent patents have significant advantages over those of the 1970s and can be practically applied to industrial production.

It is well known that, like cyclohexene, 4-VCH can be used as a hydrogen donor in catalytic transfer hydrogenation. Particularly, while serving as a hydrogen donor, 4-VCH is converted into ethylbenzene, 4-ethylcyclohexene, ethylchlorobenxane, styrene, and so on, through hydrogenation-dehydrogenation. An illustrative application of 4-VCH as a hydrogen donor is disclosed in U.S. Pat. No. 4,322,556 (1982), in which a catalytic transfer hydrogenation proceeds in the presence of iridium compound $IrCl(CO)(Ph_3P)_2$, a homogeneous catalyst, to reduce nitrobenzene into aniline.

The reaction of this patent is a homogeneous reaction which needs to react in high temperature. Further more, because the homogeneous catalyst used is composed of a precious metal, the catalyst needs to be recovered. In addition, the reaction causes a serious problem of heavy metal contamination. In fact, because environmental pollution is more serious problems than production at the present time, its industrial production is virtually impossible.

The preparation of aromatic compounds through the dehydrogenation of 4-VCH can be accomplished by either a liquid phase reaction using nitrobenzene or a gas phase reaction using metal of metal oxide. The gas phase reaction is reported in U.S. Pat. No. 5,276,257 (1994) in which ethylbenzene or styrene is prepared from 1,3-butadiene in the presence of a heterogeneous catalyst containing molybdenum. For heterogeneous catalyst, the oxide of magnesium, zinc, calcium, strontium and/or barium is also reported in U.S. Pat. No. 5,300,719 (1994). Besides these, U.S. Pat. No. 5,336,822 (1994) also discloses the preparation of styrene from 4-VCH in the presence of a heterogeneous catalyst comprising antimony by using oxygen.

Such a gas phase reaction is a heterogeneous reaction in which metals or metal oxides are used to obtain high conversion rates while maintaining high reaction temperature. Through the gas phase reaction, ethylbenzene or styrene can be obtained by subjecting 4-VCH to oxidative dehydrogenation. Such oxidative dehydrogenation through gas phase reaction is superior in reactivity and selectivity to liquid phase reaction. However, reaction temperature should be increased according to the short contact period between the catalyst and reactants. High reaction temperatures results in the short lifetime of catalysts and a lot of by-products.

SUMMARY OF THE INVENTION

It is therefore an object of the present invention to overcome the above problems encountered in prior arts and to provide a method for preparing ethylbenzene from 4-VCH, by using catalytic transfer dehydrogenation in the liquid phase. The method for preparing ethylbenzene comprises a catalytic transfer hydrogenation in which 4-VCH, in a hydrogen donor solvent, is dehydrogenated with an oxidizing agent in the presence of palladium supported on active carbon as a heterogeneous catalyst. This dehydrogenation runs at a low temperature in order to have little by-product and to obtain high conversion rates of 4-VCH.

In reducing nitrobenzene into aniline by catalytic transfer hydrogenation, 4-VCH can be converted into not only ethylbenzene but also by-products, such as 4-ethylcyclohexene, ethylcyclohexene and styrene. Intensive research has been repeated by the present inventors aiming to develop a method for preparing ethylbenzene from 4-VCH in a heterogeneous liquid phase system. Palladium supported on active carbon is a good catalyst to allow 4-VCH to be dehydrogenated into ethylbenzene on the liquid phase without by-products, such as 4-ethylcyclohexene, ethylcyclohexene and styrene. In addition, palladium supported on active carbon does not generate any problems relating to the environment, such as heavy metal, when being used to dehydrogenate 4-VCH to ethylbenzene. Particularly, the heterogeneous catalyst of the present invention is easily recovered after the catalytic transfer dehydrogenation by virtue of low reaction temperature and ordinary pressure. Such mild conditions can reduce the danger of the catalytic transfer dehydrogenation of 4-VCH to minimum level.

DETAILED DESCRIPTION OF THE INVENTION

Usually, heterogeneous catalytic reaction of the gas phase can occur under ordinary pressure. In contrast, catalytic reaction in the liquid phase does not occur under ordinary pressure without hydrogen donor solvent, such as aliphatic or aromatic alcohols and water.

The heterogeneous catalyst of the present invention, which consists of palladium supported on active carbon, allows the catalytic reaction in the liquid phase to occur under ordinary pressure. The heterogeneous catalyst has a pore size of approximately 40 $\mu$m and a specific surface area of approximately 600 m$^2$/g. Palladium is impregnated in an amount of 5% by weight in active carbon. It can catalyze both the reduction of nitrobenzene into aniline and the dehydrogenation of 4-VCH into ethylbenzene. For the latter case, 34% of 4-VCH is converted into ethylbenzene without using nitrobenzene, as will be illustrated in Example I below. It is also found that, when nitrobenzene is used in more than 0.02 mole ratio relative to 4-VCH, more than 85% of 4-VCH is dehydrogenated into ethylbenzene in the presence of the heterogeneous catalyst. However, an amount more than 0.02 mole ratio of nitrobenzene relative to 4-VCH is found to have little influence on the yield. Therefore, it is concluded that nitrobenzene not only plays the role of oxidative dehydrogenation agent, but also serves as a promoter, as will be described in detail in Example I below.

In heterogeneous catalytic reaction, water as well as alcohols can be used as a hydrogen donor solvent, thereby reducing environmental pollution and bringing about a significant economical advantage, as will be described in Example VI below. In the case of water solvent, 4-VCH is not mixed with water but the catalytic reaction is easily performed by stirring simply.

In order to know the recycle of the catalyst relating to by-products, the catalyst was repeatedly used after every reaction. Beacuse of these similar boiling points, 4-VCH and ethylbenzene cannot be separated from each other by simple distillation. For reference, the boiling points of the reactants are listed below.

| | |
|---|---|
| Ethanol | 78° C. |
| 4-VCH | 126–127° C. |
| Ethylbenzene | 136° C. |
| Aniline | 184° C. |

Thus, after 4-VCH is converted into ethylbenzene, 4-VCH and aniline are azeotropically distilled to make a reaction solution free of both 4-VCH and aniline. The recovered catalyst was reused for examining its activity with fresh 4-VCH and ethanol, as described in Example 7.

Broadly, the catalytic reaction is more advantageous in the liquid phase than in the gas phase. A significant problem of the liquid phase reaction is that, when nitrobenzene is used as an oxidizing agent, aniline which is not capable of separating from ethylbenzene is co-produced.

Sulfur and bromine are representatives of the oxidizing agents used for the dehydrogenation of cyclohexene. Upon reaction, they respectively generate hydrogen sulfide and hydrogen bromide, which are serious pollutants. In fact, sulfur and bromine can not be used for dehydrogenation agents because of the environmental pollution involved more serious problems than production.

The present inventors performed a research for an appropriate oxidizing agent that can dehydrogenated 4-VCH without causing environmental pollution. As a result, it was found the hydrogen peroxide (H$_2$O$_2$) and sodium oxychlorides (NaClO$_n$, n=1–4) can serve as good oxidizing agents. After the heterogeneous catalytic reaction, hydrogen peroxide and sodium oxychlorides are respectively converted into water and sodium chloride (NaCl), neither of which can have influence on the environment.

In particular, the good solubility of such oxidizing agents in water allows water to be used as a solvent, thereby simplifying the reaction procedure. In addition, unlike other heavy metals, the heterogeneous catalysts used in the present invention, such as palladium and platinum, do not cause the problem of environmental pollution, as described above.

Practically, hydrogen peroxide is an aqueous solution diluted 30% in water. This aqueous hydrogen peroxide solution can significantly reduce the danger of explosion as well as supply a protic solvent.

For sodium oxychlorides (NaClO$_n$, n=1–4), sodium chloride, which is almost inactive, is generated upon the catalytic transfer dehydrogenation, so that pollution is not caused. This oxidizing agent is advantageous in that water can be used as a solvent by having good compatibility therewith.

Besides nitrobenzene, hydrogen peroxide and sodium oxychloride, it was found that air or oxygen is capable of playing the role of oxidizing agents inthe dehydrogenation of 4-VCH to ethylbenzene. The dehydrogenation of 4-VCH using oxygen is already reported as disclosed in PCT No. 94/20248 and U.S. Pat. No. 5,336,822 (1994) in which 4-VCH is converted into styrene under oxygen in the presence of a heterogeneous catalyst containing tin and antimony. The reaction suggested inthe above patents is carried out at a temperature of 300 to 500° C. in the gas phase, using an excess of water which amounts to 12 to 14-fold of 4-VCH. Thus, such reaction is economically unfavorable due to the vigorous reaction condition. In addition, it is difficult to prepare the catalyst.

In accordance with the present invention, oxygen or air can be used as an oxidizing agent under mild conditions. Ethylbenzene is prepared from 4-VCH in a protic solvent, such as water or ethanol, through the liquid phase reaction using air or oxygen as an oxidizing agent, in the presence of palladium supported on active carbon. When employing air or oxygen, the reaction cannot processed in the absence of the catalyst, as will be described in detail in Example III below. The use of air or oxygen as an oxidizing agent can be accomplished by generating air bubbles with air or oxygen in a reaction suspension proceeding the reaction. Such gas-liquid reaction gives results similar to those obtained when using nitrobenzene, hydrogen peroxide or sodium chloride. The use of oxygen or air has the advantages of reducing one of the raw materials and eliminating the problems of pollution and by-product. Consequently, it is very economical.

The present invention uses advantage of typical heterogeneous catalytic reactions. The reactor used is a reactor of which the pressure can be reduced as a batch type. The products were analyzed using gas chromatography-mass selective detector (GC-MSD). Quantitative assay using gas chromatography was carried out under the conditions below:

Capillary column: ULTRA I (crosslinked methylsilicone Gum) 50 m×0.22 mm×0.33 μm

Carrier : nitrogen

Head pressure : 18 psig

Oven : 120° C. (2 min) to 250° C. β=5° C./min

Injection Temp. : 200° C.

Detector & Temp. : FID (280° C.)

Split ratio : 50:1

Makeup gas flowrate: 38 ml

For a component ratio, the area ratio was calculated and utilized.

A better understanding of the present invention may be obtained in light by the following examples which are set forth to illustrate the present invention. These examples are constructed to limit the scope and spirit of the present invention.

EXAMPLE I

In a 100 ml 3-neck flask which could allow distillation under reduced pressure and equipped with a cooler, 4-VCH (10.80 g, 100 mmole), the amount of nitrobenzene given in Table 1, and 2 g of palladium (5 wt %)/active carbon catalyst in ethanol (4.4 ml, 75 mmole) was refluxed for one hour. The suspension was filtered and the resulting filtrate was analyzed by gas chromatography. The results are given as shown in Table 1 below.

TABLE 1

Yields Depending on Mole Ratio of Nitrobenzene to 4-VCH

| Nitrobenzene (Mole Ratio) | Aniline (Yield %) | 4-VCH/Ethylbenzene/By-Product (Yield %) |
|---|---|---|
| 0 | 0 | 66/34/0 |
| 0.01 | 87 | 1/75/24 |
| 0.02 | 95 | 0/85/15 |
| 0.1 | 100 | 1/86/13 |
| 0.5 | 35 | 0/88/12 |
| 1.0 | 9 | 0/87/13 |

As shown in Table 1, the yield of ethylbenzene from 4-VCH without nitrobenzene was 34%. When 0.01 mole ratio of nitrobenzene to 4-VCH was added, the yield of ethylbenzene significantly increased to 75%. However, even when using 0.5 or 1 mole ratio of nitrobenzene to 4-VCH, the yield was almost the same.

EXAMPLE II

The procedure of Example I was repeated using 1:0.1 mole ratio of 4-VCH to nitrobenzene while changing the reaction temperatures. The results of the gas chromatography analysis are given as shown in Table 2 below.

TABLE 2

Yield Depending on Reaction Temperature

| Reaction Temp. (°C.) | Aniline (Yield %) | 4-VCH/Ethylbenzene/ By-Product (Yield %) |
|---|---|---|
| 50 | 0 | 100/0/0 |
| 65 | 0 | 100/0/0 |
| 78 | 100 | 1/86/13 |

EXAMPLE III

The procedure of Example I was repeated using 1:0.1 mole ratio of 4-VCH to nitrobenzene while changing the amount of the catalyst, palladium (5 wt %)/active carbon. The results of the gas chromatography analysis are given as shown in Table 3 below.

TABLE 3

Yield Depending on the Amount of Catalyst

| Amount of Catalyst (g) | Aniline (Yield %) | 4-VCH/Ethylbenzene/By-Product (Yield %) |
|---|---|---|
| 0 | — | 100/0/0 |
| 1 | 36 | 36/48/16 |
| 2 | 100 | 1/86/13 |
| 3 | 100 | 1/86/13 |

As apparent from Table 3, the reaction did not proceed in the absence of the catalyst. Table 3 also shows that even an amount larger than 2 g of the catalyst can not bring about an improvement in yield.

EXAMPLE IV

The procedure of Example I was repeated using 1:0.1 mole ratio of 4-VCH to nitrobenzene while changing the mole ratio of ethanol, the hydrogen donor, to nitrobenzene. The results of the gas chromatography analysis are given as shown in Table 4 below.

TABLE 4

Yields Depending on the Mole ratio of Nitrobenzene to Ethanol

| Nitrobenzene/EtOH (Mole Ratio) | Aniline (Yield %) | 4-VCH/Ethylbenzene/By-Product (Yield %) |
|---|---|---|
| 1/3.2 | 79 | 13/77/10 |
| 1/6.4 | 100 | 7/82/11 |
| 1/7.5 | 100 | 1/86/13 |

EXAMPLE V

The procedure of Example I was repeated using 1:0.1 mole ratio of 4-VCH to nitrocompounds listed in Table 5 below.

The results of the gas chromatography analysis are given as shown in Table 5 below.

TABLE 5

Yields Depending on Nitrocompounds

| Nitrocompounds (Yield %) | Amines (Yield %) | 4-VCH/Ethylbenzene/ By-Product |
|---|---|---|
| nitrobenzene | aniline (100) | 1/86/13 |
| p-dinitrobenzene | p-diaminobenzene | 1/89/10 |
| 4-nitrotoluene | 4-aminotoluene | 2/86/12 |
| nitromethane | methylamine* | 22/67/11 |

*yield did not determine owing to low b.p (40° C.)

EXAMPLE VI

The procedure of Example I was repeated using 1:0.1 mole ratio of 4-VCH to nitrobenzene and using water, instead of ethanol, as a solvent while changing the mole ratio of nitrobenzene to water.

The results of the gas chromatography analysis are given as shown in Table 6 below.

TABLE 6

Yields Depending on the Mole Ratio of Nitrobenzene to Water

| Nitrobenzene/Water (Mole Ratio) | Aniline (Yield %) | 4-VCH/Ethylbenzene/ By-Product (Yield %) |
|---|---|---|
| 1/2.7 | 100 | 10/75/15 |
| 1/7.5 | 100 | 10/75/15 |
| 1/15 | 100 | 7/83/10 |
| 1/30 | 100 | 6/83/11 |

EXAMPLE VII

In a 100 ml 3-neck flask which could allow distillation under reduced pressure and equipped with a cooler, 5.40 g (100 mmole) of 4-VCH and 41.2 ml (49.2 g, 400 mmole) of nitrobenzene were dissolved in 17.6 ml (13.80 g, 300 mmole) of ethanol. 7 g of palladium (5 wt %)/active carbon catalyst was added to the solution, resulting in a suspension. The suspension was refluxed for one hour and cooled to room temperature. The catalyst was filtered off and the filtrate was distilled to separate ethylbenzene from ethanol. The reside was added with the same amounts of fresh 4-VCH and ethanol. These reactants were let to react in the presence of the reclaimed catalyst.

Again, the same procedure was repeated. The filtrates after every procedure were subjected to gas chromatography, to analyze the reactivity of the catalyst. The results are given as shown in Table 7 below.

TABLE 7

Reactivity of the Recovered Catalyst

| recycle | 4-VCH/Ethylbenzene/By-Product (Yield %) |
|---|---|
| 1st | 1/94/5 |
| 2nd | 4/90/6 |
| 3rd | 28/70/2 |

EXAMPLE VIII

In a 100 ml 3-neck flask which could allow distillation under reduced pressure and equipped with a cooler and a dropping funnel, 10.80 g (100 mmole) of 4-VCH and 2 g of palladium (5 wt %)/active carbon catalyst were placed and heated up to 95° C. while stirring, to give suspension. 22.5 ml (200 mmole) of the aqueous solution of 30% hydrogen peroxide ($H_2O_2$) was slowly dropwise added through the funnel into the flask which was maintained at 95° C. After being refluxed for 1 hour, the reaction solution was analyzed. Gas chromatography showed that 4-VCH was converted to ethylbenzene at 71% and the unreacted 4-VCH remained at 9% while by-product was formed at 20%.

EXAMPLE IX

The procedure of Example VIII was repeated except that the amount of hydrogen peroxide was changed as indicated in Table 8 below.

TABLE 8

Yield Depending on Amount of Hydrogen Peroxide

| Amount of $H_2O_2$ (ml/mmole) | 4-VCH/Ethylbenzene/By-Product (Yield %) |
|---|---|
| — | 66/34/0 |
| 11.8/100 | 29/90/6 |
| 22.5/200 | 9/71/20 |
| 33.7/300 | 14/66/20 |

As shown in Table 8, it is most favorable to use hydrogen peroxide at the equivalent of 4-VCH.

EXAMPLE X

The procedure of Example VIII was repeated using the catalyst at different amounts as indicated in Table 9 below.

TABLE 9

Yield Depending on Amount of Catalyst

| Amount of Catalyst (g) | 4-VCH/Ethylbenzene/By-Product (Yield %) |
|---|---|
| 2 | 9/71/20 |
| 3 | 13/87/0 |

The amount of the by-product was reduced, as the amount of the catalyst was large.

EXAMPLE XI

In a 100 ml 3-neck flask which could allow distillation under reduced pressure and equipped with a cooler and a dropping funnel, 10.80 g (100 mmole) of 4-VCH and 2 g of palladium (5wt %)/active carbon catalyst were placed and heated up to 95° C. while stirring, to give suspension. The solution of 7.4 g (100 mmole) of sodium hypochlorous acid (NaOCl) in 3.6 g (200 mmole) of water was slowly dropwise added through the funnel into the flask which was maintained at 95° C. After being refluxed for 1 hour, the reaction solution was filtered to remove the catalyst, and then analyzed. Gas chromatography showed that 4-VCH was converted to ethylbenzene at 72% and the unreacted 4-VCH remained at 26% while by-product was formed at 2%.

EXAMPLE XII

The procedure of Example XI was repeated except that the amount of water was changed as indicated in Table 10 below.

TABLE 10

Yield Depending on Amount of Water

| Amount of Water (g/mmole) | 4-VCH/Ethylbenzene/By-Product (Yield %) |
|---|---|
| 0.9/50 | 42/40/18 |
| 1.8/100 | 43/38/19 |
| 3.6/200 | 26/72/2 |

As shown in Table 10, it is most favorable to use water at the equivalent of twice as much water as 4-VCH.

EXAMPLE XIII

The procedure of Example XI was repeated using different amounts of NaOCl as indicated in Table 11 below.

TABLE 11

Yield Depending on Amount of NaOCl

| Mole No. of NaOCl (mmol) | 4-VCH/Ethylbenzene/By-Product (Yield %) |
|---|---|
| 25 | 13/62/25 |
| 50 | 5/71/24 |
| 100 | 26/72/2 |
| 200 | 3/77/20 |

EXAMPLE XIV

The procedure of Example XI was repeated using oxidizing agents indicated in Table 12 below.

TABLE 12

Yield Depending on Various Oxidizing Agents

| Oxidizing Agents | 4-VCH/Ethylbenzene/By-Product (Yield %) |
|---|---|
| NaOCl | 26/72/2 |
| NaClO$_2$ | 48/44/8 |
| NaClO$_3$ | 2/80/18 |
| NaClO$_4$ | 21/68/11 |

EXAMPLE XV

The procedure of Example XI was repeated except that the reaction temperature was changed as indicated in Table 13 below.

TABLE 13

Yield Depending on Reaction Temperature

| Reaction Temp. | 4-VCH/Ethylbenzene/By-Product (Yield %) |
|---|---|
| 50 | 100/—/— |
| 80 | 75/18/7 |
| 100 | 26/72/2 |

EXAMPLE XVI

The procedure of Example XII was repeated using ethanol as a reaction solvent.

TABLE 14

Yield Depending on Oxidizing Agents

| Oxidizing Agents | 4-VCH/Ethylbenzene/By-Product (Yield %) |
|---|---|
| NaOCl | 6/74/20 |
| NaClO$_2$ | 100/—/— |
| NaClO$_3$ | 12/70/18 |
| NaClO$_4$ | 6/76/18 |

EXAMPLE XVII

In a 100 ml 3-neck flask which could allow distillation under reduced pressure and equipped with a cooler and a dropping funnel, 10.80 g (100 mmole) of 4-VCH and 2 g of palladium (5 wt %)/active carbon catalyst were dissolved in 3.45 g (75 mmole) of ethanol and rised to the reflux temperature while stirring, to give suspension. It was refluxed for 1 hour while oxygen was injected. Thereafter, the catalyst was filtered off and the resulting solution was analyzed. Gas chromatography showed that 4-VCH was converted to ethylbenzene at 79% and the unreacted 4-VCH remained at 5% while by-product was formed at 16%.

EXAMPLE XVIII

The procedure of Example XVII was repeated except that, instead of oxygen, air was used as an oxidizing agent. Gas chromatography showed that 4-VCH was converted to ethylbenzene at 77% and the unreacted 4-VCH remained at 12% while by-product was formed at 11%.

EXAMPLE XIX

The procedure of Example XVII was repeated except that, instead of ethanol, water was used as a solvent. Gas chromatography showed that 4-VCH was converted to ethylbenzene at 78% and the unreacted 4-VCH remained at 22%.

EXAMPLE XX

The procedure of Example XVIII was repeated except that, instead of ethanol, water was used as a solvent. Gas chromatography showed that 4-VCH was converted to ethylbenzene at 7% and the unreacted 4-VCH remained at 8 while by-product was formed at 24%.

The present invention has been described in an illustrative manner, and it is to be understood that the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A method for preparing ethylbenzene comprising subjecting 4-vinylcyclohexene to a catalytic transfer hydrogenation, in which 4-vinylcyclohexene in a hydrogen donor solvent is dehydrogenated with an oxidizing agent in the presence of palladium supported on active carbon as a heterogeneous catalyst.

2. A method according to claim 1, wherein said palladium catalyst is used in an amount of 0.5 to 10% by weight based on the weight of 4-vinylcyclohexene.

3. A method according to claim 1, wherein said catalytic transfer hydrogenation is carried out at a temperature of 50 to 110° C.

4. A method according to claim 1, wherein said hydrogen donor solvent is selected from the group consisting of alcohols, water, and a mixture of there.

5. A method according to claim 1, wherein said oxidizing agent is selected from the group consisting of nitro compounds, hydrogen peroxide, sodium oxychlorides ($NaClO_n$, n=1–4), oxygen, and air.

6. A method according to claim 5, wherein said hydrogen peroxide as the oxidizing agent is used in an amount of 1 to 3 moles per mole of 4-vinylcyclohexene.

7. A method according to claim 5, wherein said nitro compounds are selected from the group consisting of nitromethane, nitrobenzene, nitrotoluene, and dinitrobenzene.

8. A method according to claim 5, wherein said nitro compounds are used in an amount of 0.02 to 0.5 mole per mole of 4-vinylcyclohexene.

9. A method according to claim 5, wherein said sodium oxychlorides are selected from the group of sodium salts of hypochlorite acid, chlorite acid, chlorate and perchlorate.

10. A method according to claim 5, wherein said sodium chlorides are used in an amount of 0.5 to 3 moles per mole of 4-vinylcyclohexene.

* * * * *